United States Patent [19]

Kerschner et al.

[11] Patent Number: 5,256,779
[45] Date of Patent: Oct. 26, 1993

[54] SYNTHESIS OF MANGANESE OXIDATION CATALYST

[75] Inventors: Judith L. Kerschner, Ridgewood; Lisa DelPizzo, Bloomfield, both of N.J.

[73] Assignee: Lever Brothers Company, Division of Conopco, Inc., New York, N.Y.

[21] Appl. No.: 900,861

[22] Filed: Jun. 18, 1992

[51] Int. Cl.$^5$ .................... B01J 31/22; C07D 255/02
[52] U.S. Cl. ............................ 540/465; 502/150; 502/160; 502/167
[58] Field of Search ............... 540/465; 502/150, 160, 502/167

[56] References Cited

U.S. PATENT DOCUMENTS

| | | | |
|---|---|---|---|
| 4,728,455 | 3/1988 | Rerek | 252/99 |
| 5,153,161 | 10/1992 | Kerschner et al. | 502/167 |

FOREIGN PATENT DOCUMENTS

| | | | |
|---|---|---|---|
| 0306089 | 3/1989 | European Pat. Off. | 540/201 |
| 0369841 | 5/1990 | European Pat. Off. | 252/99 |
| 0458397 | 11/1991 | European Pat. Off. | 502/167 |
| 0458398 | 11/1991 | European Pat. Off. | 502/167 |

OTHER PUBLICATIONS

K. Wieghardt, "Journal of the American Chemical Society", 1988, vol. 110, No. 22, p. 7398.
"Journal of the Chemical Society—Chemical Communications", 1985, p. 1145.

*Primary Examiner*—Robert T. Bond
*Attorney, Agent, or Firm*—Milton L. Honig

[57] ABSTRACT

A process is described for the preparation of a compound having the formula:

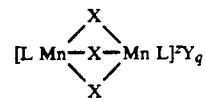

wherein Mn is manganese in a III or IV oxidation state;
X is independently selected from a coordinating or bridging species selected from the group consisting of:
$H_2O$, $O_2^{2-}$, $O_2^-$, $OH^-$, $HO_2^-$, $SH^-$, $S^{2-}$, $SO$, $Cl^-$, $N_3^-$, $SCN^-$, $N^{3-}$, $HCOO^-$, $NH_2^-$ and $NH_3$;
L is an organic ligand that is at least a nine-membered ring wherein at least two nitrogen atoms form part of the ring and coordinate with the Mn;
z is an integer ranging from $-4$ to $+4$;
Y is a monovalent or multivalent counterion leading to charge neutrality selected from the group consisting of halides, sulphates, sulphonates, nitrates, boron and phosphorus salt counterions; and
q is an integer from 1 to 4;
the process comprising the steps of:
(i) reacting in an aqueous medium a manganese (II) salt with the ligand L to form a manganese coordinated substance, a counterion salt $M_zY_q$ being present wherein M is selected from the group consisting of metallic and ammonium ions; and
(ii) oxidizing the manganese coordinated substance with an oxidizing agent while simultaneously maintaining a pH of at least 12 to thereby form the compound.

8 Claims, No Drawings

SYNTHESIS OF MANGANESE OXIDATION CATALYST

BACKGROUND OF THE INVENTION

1. Field of the Invention

The invention concerns an improved synthesis of a manganese complex useful as a bleach catalyst.

2. The Related Art

Peroxide bleaching agents for use in laundering have been known for many years. Such agents are effective in removing stains, such as tea, fruit and wine stains, from clothing at or near boiling temperatures. The efficacy of peroxide bleaching agents diminishes sharply at temperatures below 60° C.

It is known that many transition metal ions catalyze the decomposition of $H_2O_2$ and $H_2O_2$-liberating percompounds, such as odium perborate. It has also been suggested that transition metal salts together with a chelating agent be employed to activate peroxide compounds to render them usable for satisfactory bleaching at lower temperatures. Not all combinations of transition metals with chelating agents are suitable for improving the bleaching performance of peroxide compound bleaches. Many combinations indeed show no effect, or even a worsening effect, on the bleaching performance. A recent advance in this technology was reported in EP 0 458 397 and EP 0 458 398 which describe a class of highly active bleaching catalysts in the form of a manganese complex having the general formula:

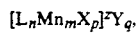

and especially the species:

Several of the aforementioned complexes were first synthesized and described by K. Wieghardt in the "Journal of the American Chemical Society", 1988, Vol. 110, No. 22, page 7398, as well as in the "Journal of the Chemical Society—Chemical Communications", 1985, page 1145.

The synthesis route as described in the above art involves the reaction in aqueous medium of a manganese (III)-compound, e.g. Mn (III)-triacetate, with a proper nitrogen-containing ligand, e.g. 1,4,7-trimethyl-1,4,7-triazacyclononane, using an ethanol/water mixture as the solvent. A drawback of the aforementioned process is that only low yields of the dinuclear Mn (III)-complex can be achieved. Another problem associated with the process of the art is that, owing to the slow crystallization of the product, long reaction times are necessary. Still another problem is that besides crystallization of the desired product, decomposition also seems to occur, yielding manganese dioxide which contaminates the product. Therefore, a purification process is required when the product is to be converted into the dinuclear Mn (IV)-complex.

More recently there was reported a process for the preparation of manganese complex catalysts, U.S. Pat. No. 5,153,161 issued Oct. 6, 1992, wherein a four-step procedure was outlined. Therein a manganese II salt and a ligand L were reacted to form a manganese coordinated substance. In a second and third step, the substance is oxidized and then basified to a pH of at least 10.5, respectively. The fourth step requires contacting the basified reaction mixture with a further oxidizing agent so as to form the final manganese complex catalyst. Yields in the 60% range are thereby achieved. Improvements in yield and reduction in processing costs would be desirable.

Accordingly, it is an object of the present invention to provide an improved method for the preparation of manganese (III)- and manganese (IV)-dinuclear complexes.

A more specific object of the present invention is to provide an improved method for preparing manganese complexes of high purity in high yields, which can be converted into the corresponding dinuclear manganese (IV)-complexes by oxidation.

These and other objects of the present invention will become more readily apparent from the detailed description and examples given hereafter.

SUMMARY OF THE INVENTION

A process is described for the preparation of a compound having the formula:

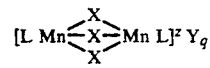

wherein

Mn is manganese in a III or IV oxidation state;

X is independently selected from a coordinating or bridging species selected from the group consisting of:
$H_2O$, $O_2^{2-}$, $O_2^-$, $OH^-$, $HO_2^-$, $SH^-$, $S^{2-}$, $SO$, $Cl^-$, $N_3^-$, $SCN^-$, $N^{3-}$, $HCOO^-$, $NH_2^-$ and $NH_3$;

L is an organic ligand that is at least a nine-membered ring wherein at least two nitrogen atoms form part of the ring and coordinate with the Mn;

z is an integer ranging from $-4$ to $+4$;

Y is a monovalent or multivalent counterion leading to charge neutrality selected from the group consisting of halides, sulphates, sulphonates, nitrates, boron and phosphorus salt counterions; and q is an integer from 1 to 4;

the process comprising the steps of:

(i) reacting in an aqueous medium a manganese (II) salt with the ligand L to form a manganese coordinated substance, a counterion salt $M_zY_q$ being present wherein M is selected from the group consisting of metallic and ammonium ions; and (ii) oxidizing the manganese coordinated substance with an oxidizing agent while simultaneously maintaining a pH of at least 12 to thereby form the compound.

DETAILED DESCRIPTION

Now it has been found that high yields of dinuclear manganese complexes of relatively high purity can be obtained at a much shorter reaction time and essentially, in a single pot reaction through use of simple manganese (II) inorganic salts.

Accordingly, in its broadest aspect, the invention provides a process for preparation of dinuclear manganese complexes of the formula:

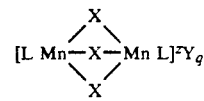

wherein

Mn is manganese in a III or IV oxidation state;

X is independently selected from a coordinating or bridging species selected from the group consisting of: $H_2O$, $O_2^{2-}$, $O_2^-$, $OH^-$, $HO_2^-$, $SH^-$, $S^{2-}$, $SO$, $Cl^-$, $N_3^-$, $SCN^-$, $N^{3-}$, $HCOO^-$, $NH_2^-$ and $NH_3$;

L is an organic ligand containing at least two nitrogen atoms that coordinate with the Mn;

z is an integer ranging from −4 to +4;

Y is a monovalent or multivalent counterion leading to charge neutrality; and q is an integer from 1 to 4.

The counterion Y needed for charge neutrality of the complex is generally provided by carrying out the complexation reaction in the presence of a counterion-forming salt. Though the type of the counterion-forming salt, e.g. chlorides; sulphates; nitrates; methylsulphates; and surfactants such as alkyl sulphates, alkyl sulphonates, alkylbenzene sulphonates, tosylates, trifluoromethyl sulphonates, perchlorates, $NaBH_4$ and $KPF_6$, is not critical for the conversion, some salts are more preferred than others in terms of product properties or safety. For example, small counterions will produce oily liquids and perchlorates are potentially explosive and could become a severe hazard upon large-scale preparation. Preferred counterions are the large molecules from surfactants, especially tosylate. A particularly preferred counterion is $PF_6^-$, which is conveniently obtained from $KPF_6$. Dinuclear manganese (III) and manganese (IV) complexes having $PF_6^-$ as the counterion, are solid crystalline products which are easy to handle and to form into a granulated catalyst product. Even more preferred is sulfate as counterion.

Suitable and preferable ligands for use in the present invention are those which coordinate the three nitrogen atoms to one of the manganese centers, preferably being of a macrocyclic nature.

The nitrogen atoms can be part of tertiary, secondary or primary amine groups, but also part of aromatic ring systems, e.g. pyridines, pyrazoles, etc. or combinations thereof.

Examples of specific ligands most preferred are those having the structures:

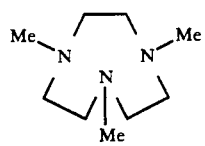

I

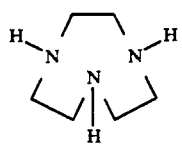

II

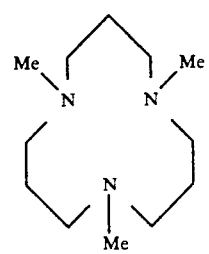

III

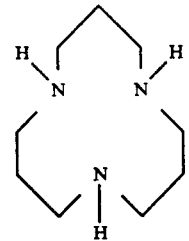

IV

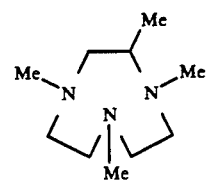

V

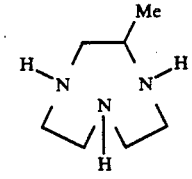

VI

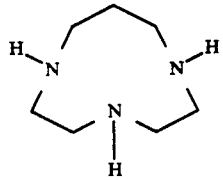

VII

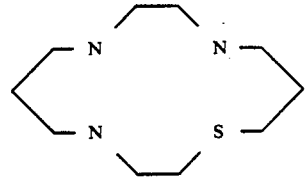

VIII

The most preferred ligands are I–V, with I being particularly preferred.

Ligand (I) is 1,4,7-trimethyl-1,4,7-triazacyclononane, coded as Me-TACN; ligand (II) is 1,4,7-triazacyclononane, coded as TACN; ligand (III) is 1,5,9-trimethyl-1,5,9-triazacyclododecane, coded as Me-TACD; ligand (V) is 2-methyl-1,4,7-trimethyl-1,4,7-triazacyclononane, coded as Me/Me-TACN; and ligand (VI) is 2-methyl-1,4,7-triazacyclononane, coded as Me/TACN.

Any of these complexes, either preformed or formed in situ during the washing process, are useful catalysts for the bleach activation of peroxy compounds over a wide class of stains at lower temperatures in a much more effective way than the Mn-based catalysts of the art hitherto known. Furthermore, these catalysts exhibit a high stability against hydrolysis and oxidation, even in the presence of oxidants such as hypochlorite.

Manganese complexes which are the object of the present synthesis and which are particularly preferred are those with the following structures:

$[LMn(IV)(\mu-O)_3Mn(IV)L]^z Y_q$ wherein L, Y, q and z are as described above.

Specifically preferred is a compound of the structure:

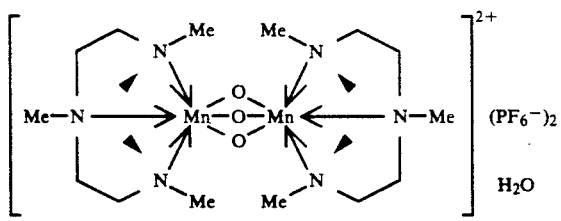

abbreviated as [Mn$^{IV}$$_2$($\mu$-O)$_3$(Me-TACN)$_2$](PF$_6$)$_2$.H$_2$O.

An important advantage of the process according to the invention is that it can be performed in a single reactor without isolation of any intermediate products as was heretofor required. A first step of the process involves reacting a manganese (II) salt with a ligand L in the presence of a counterion salt M$_z$Y$_q$. Suitable as manganese (II) salts are manganese chloride, manganese sulphate, manganese bromide and manganese nitrate, with the manganese chloride being preferred.

The molar ratio of manganese (II) salt to ligand may range anywhere from 4:1 to 1:2, preferably from about 2:1 to about 1:1, optimally about 1.5:1 to 1:1. Relative molar ratios of the manganese (II) salt to the counterion salt will range from about 4:1 to 1:4, preferably from about 2:1 to about 1:2, optimally between about 1:1 and 1:2. In a second and final step of the reaction, the manganese coordinated substance formed in the first step is oxidized. Oxidation can be performed with air, pure oxygen, hydrogen peroxide, potassium permanganate or any combination thereof. Most preferred, however, as an oxidizing agent is aqueous hydrogen peroxide or solid sodium peroxide.

In the second step of the reaction, the reaction medium must be held at a pH of at least 12. Sodium hydroxide is the preferred basifying agent. It is important that the reaction mixture of the second step simultaneously be provided with both the oxidizing and the basifying agents. Only under such circumstances will high and reproducible yields be achieved.

Advantageously, upon reaction completion the resultant mixture is quenched by lowering pH to 9 or below, preferably between 7 and 9. Decomposition of the desired manganese complex catalyst is thereby avoided.

For purposes of this invention, there need be no isolation of any coordinated manganese intermediates. In fact, such isolation of a coordinated manganese intermediate is disadvantageous. Further, for purposes of this invention it is advantageous to employ a protic solvent system. Particularly useful is a combination of a C$_1$-C$_4$ alkanol and water in a ratio of about 10:1 to 1:10, preferably 4:1 to 1:1, optimally about 2:1. The preferred alkanol is ethanol.

With the process of this invention it is no longer necessary nor desirable that between formation of a manganese coordinated substance and before basification that a preliminary oxidation occur. Under the process of the present invention, the intermediate oxidation is eliminated and basification with final oxidation is performed concurrently in a single step.

The following examples will more fully illustrate the embodiments of this invention. All concentrations presented are by weight unless otherwise indicated.

EXAMPLE 1

Synthesis of Mn$_2$(MeTACN)$_2$($\mu$-O)$_3$(PF$_6$)$_2$ via Mn(II) Salts and Sodium Peroxide In a 2L round-bottom flask was dissolved 18.4 g MnCl$_2$ (0.146 mole) in 1000 ml ethanol/water (67:33). To the resultant solution under agitation was then added 25 g MeTACN (0.146 mole) and 26 g NaPF$_6$ (0.156 mole). This solution was stirred at room temperature for 20 minutes and then was chilled to about 5° C. in an ice bath. To the stirring, chilled solution was slowly added (over 3 minutes) 10.75 g of solid sodium peroxide (0.146 mole). The pH of the solution was greater than 12. After complete addition of the sodium peroxide, the reaction mixture was stirred surrounded by an ice bath for one hour and then warmed to room temperature. The mixture was stirred at room temperature for an additional 45 minutes. Finally, the reaction mixture pH was lowered to 8-9 with 1.2N sulfuric acid and filtered through a medium porosity glass frit to remove the manganese by-product and washed with water until the filter pad rinsed colorless (to remove any red precipitated Mn(IV) product). The cherry red solution was then concentrated to 1/10 the original solvent volume causing crystallization of the product. This concentrated solution was filtered and the red crystalline product was washed with ethanol (25 ml) and dried under vacuo. Yield was 34.8 g Mn(IV)$_2$(MeTACN)$_2$($\mu$-O)$_3$(PF$_6$)$_2$.H$_2$O (Purity=97%).

EXAMPLE 2

Synthesis of Mn$_2$(MeTACN)$_2$($\mu$-O)$_3$(PF$_6$)$_2$ via Mn(II) Salts and Hydrogen Peroxide In a 2 L round bottomed flask was dissolved 11.1 g MnCl$_2$ (0.088 mole) in 600 ml ethanol/water (67:33). To this stirring solution was then added 15 g MeTACN (0.088 mole) and 17.5 g KPF$_6$ (0.095 mole). This solution was stirred at room temperature for 20 minutes and then was chilled to about 5° C. in an ice bath. To the stirring, chilled solution was slowly added (over 3 minutes) a premixed water solution of one mole equivalent hydrogen peroxide (3%) and 1.5 mole equivalents sodium hydroxide (20% aqueous solution). This corresponds to adding a mixture of 99 ml of hydrogen peroxide (3%) and 26.3 ml sodium hydroxide (20% solution) to the reaction mixture. The pH of the solution was greater than 12. After complete addition of the peroxide premix, the resultant reaction mixture was stirred surrounded by an ice bath for one hour and then warmed to room temperature. The mixture was stirred at room temperature for an additional 45 minutes. Finally, the reaction mixture pH was lowered to 8-9 with 1.2N sulfuric acid and filtered through a medium porosity glass frit to remove the manganese byproduct and washed with water until the filter pad rinsed colorless (to remove any red precipitated Mn(IV) product). The cherry red solution was then concentrated to 1/10 the original solvent volume causing crystallization of the product. This concentrated solution was filtered and the red crystalline product was washed with ethanol (25 ml) and dried under vacuo. Yield was 25.8 g Mn(IV)$_2$(MeTACN)$_2$($\mu$-O)$_3$(PF$_6$)$_2$.H$_2$O (Purity=97%).

EXAMPLE 3

Comparison of Various Oxidizing Agents

Various combinations of oxidizing agents have been used to prepare $Mn_2(MeTACN)_2(\mu\text{-}O)_3(PF_6)_2$ and the results of these preparations are recorded in the following table. The first three entries were performed via two oxidation steps. The first oxidation was performed at pH=7. Thereafter, the pH was raised to greater than 10.5 with triethyl amine whereupon the second oxidation was performed. The last two entries report results deriving from Examples 1 and 2.

| Oxidizing Agent | | Purity | Yield | Rxn. Time |
| --- | --- | --- | --- | --- |
| 1st Step | 2nd Step | | | |
| $O_2$ | $O_2$ | 38% | 39% | 5 hrs. |
| $KMnO_4$ | $KMnO_4$ | 70% | 50% | 3 hrs. |
| $H_2O_2$ | $O_2$ | 70% | 60% | 3 hrs. |
| $Na_2O_2$ | (one step) | 100% | 72% | 2 hrs. |
| $H_2O_2/NaOH$ | (one step) | 100% | 74% | 2 hrs. |

EXAMPLE 4

The synthesis can be performed with a variety of Mn(II) salts to produce $Mn_2(MeTACN)_2(\mu\text{-}O)_3(PF_6)_2$. Results obtained with two specific Mn(II) compounds are shown in the following table.

| Starting Material | Purity | Yield |
| --- | --- | --- |
| $MnCl_2$ | 100% | 74% |
| $MnSO_4$ | 90% | 65% |

EXAMPLE 5

Simultaneous addition of the base and peroxide has been found to produce higher yields of the desired product than subsequent addition of the two reactants. As shown in the following table, addition of sodium peroxide or a $NaOH/H_2O_2$ mixture (pH greater than 12) gives more product than addition of $H_2O_2$ followed by addition of NaOH (pH greater than 12) or vice versa.

| | Purity | Yield |
| --- | --- | --- |
| 1. Addition of $H_2O_2$ then NaOH | 55% | <40% |
| 2. Addition of NaOH then $H_2O_2$ | — | <10% |
| 3. Addition of $H_2O_2/NaOH$ mixture | 100% | 74% |
| 4. Addition of sodium peroxide | 100% | 72% |

The foregoing description and examples illustrate selected embodiments of the present invention. In light thereof, various modifications will be suggested to one skilled in the art, all of which are within the spirit and purview of this invention.

What is claimed is:

1. A process for the preparation of a compound having the formula:

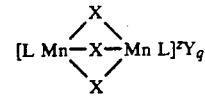

wherein

Mn is manganese in a III or IV oxidation state;

X is independently selected from a coordinating or bridging species selected from the group consisting of:

$H_2O$, $O_2^{2-}$, $O_2-$, $OH^-$, $HO_2^-$, $SH^-$, $S^{2-}$, $SO$, $Cl^-$, $N_3^-$, $SCN^-$, $N^{3-}$, $HCOO^-$, $NH_2^-$ and $NH_3$;

L is an organic ligand that is at least a nine-membered ring wherein at least two nitrogen atoms form part of the ring and coordinate with the Mn;

z is an integer ranging from $-4$ to $+4$;

Y is a monovalent or multivalent counterion leading to charge neutrality selected from the group consisting of halides, sulphates, sulphonates, nitrates, boron and phosphorus salt counterions; and q is an integer from 1 to 4;

the process comprising the steps of:

(i) reacting in an aqueous medium a manganese (II) salt with the ligand L to form a manganese coordinated substance, a counterion salt $M_zY_q$ being present wherein M is selected from the group consisting of metallic and ammonium ions; and (ii) oxidizing the manganese coordinated substance with an oxidizing agent while simultaneously maintaining a pH of at least 12 to thereby form the compound.

2. A method according to claim 1 wherein the pH is at least 12.5.

3. A method according to claim 1 wherein the oxidizing agent is selected from the group consisting of hydrogen peroxide and sodium peroxide.

4. A method according to claim 1 wherein basification is achieved with sodium hydroxide.

5. A method according to claim 1 wherein the compound has the formula $[LMn(IV)(\mu\text{-}O)_3Mn(IV)L]^zY_q$.

6. A method according to claim 1 wherein the compound has the formula $[Mn^{IV}_2(\mu\text{-}O)_3(Me\text{-}TACN)_2](PF_6)_2 \cdot H_2O$.

7. A method according to claim 1 wherein the compound has the formula $[Mn^{IV}_2(\mu\text{-}O)_3(Me\text{-}TACN)_2](SO_4)$.

8. A method according to claim 1 wherein subsequent to step (ii) and formation of the compound, the pH of the aqueous medium is quenched to a level no higher than pH 9 and thereafter the compound is separated as a solid from the aqueous medium.

* * * * *